United States Patent
Fukae et al.

(10) Patent No.: US 8,404,922 B2
(45) Date of Patent: Mar. 26, 2013

(54) ABSORBENT ARTICLE AND METHOD OF PRODUCING THE SAME

(75) Inventors: Akinori Fukae, Shikokuchuo (JP); Yumiko Seike, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 937 days.

(21) Appl. No.: 12/083,190

(22) PCT Filed: Oct. 6, 2006

(86) PCT No.: PCT/JP2006/320107
§ 371 (c)(1),
(2), (4) Date: Aug. 5, 2008

(87) PCT Pub. No.: WO2007/043474
PCT Pub. Date: Apr. 19, 2007

(65) Prior Publication Data
US 2009/0137977 A1    May 28, 2009

(30) Foreign Application Priority Data

Oct. 7, 2005 (JP) ................................. 2005-295484
Oct. 25, 2005 (JP) ................................. 2005-309445

(51) Int. Cl.
*A61F 13/15* (2006.01)
*A61F 13/20* (2006.01)

(52) U.S. Cl. .................... 604/380; 604/385.01; 604/379

(58) Field of Classification Search ............. 604/385.01, 604/385.101, 367, 378–380
See application file for complete search history.

(56) References Cited

U.S. PATENT DOCUMENTS

| | | | |
|---|---|---|---|
| 6,203,654 B1 * | 3/2001 | McFall et al. | 156/268 |
| 6,586,076 B1 * | 7/2003 | Mizutani et al. | 428/173 |

FOREIGN PATENT DOCUMENTS

| | | | |
|---|---|---|---|
| CN | 1159318 A | | 9/1997 |
| CN | 1294904 A | | 5/2001 |
| CN | 1349789 A | | 5/2002 |
| EP | 0 007 665 | * | 2/1980 |
| JP | H03-111198 A | | 5/1991 |
| JP | H05-228173 A | | 9/1993 |
| JP | 09-234221 | | 9/1997 |
| JP | 10-211232 | | 8/1998 |
| JP | 2001-095845 | | 4/2001 |
| JP | 2002-105835 | | 4/2002 |
| JP | 2002-187228 | | 7/2002 |
| JP | 2003-250836 | | 9/2003 |
| JP | 2004-298454 | | 10/2004 |
| JP | 2005-152241 | | 6/2005 |
| JP | 2005-218648 | | 8/2005 |
| JP | 2001-137284 A | | 5/2011 |

* cited by examiner

*Primary Examiner* — Michele M Kidwell
(74) *Attorney, Agent, or Firm* — DLA Piper LLP (US)

(57) ABSTRACT

An absorbent article comprising a face sheet and an absorbent body in this order, wherein the face sheet is at least one of concavo-convex or convexo-flat heat-embossed sheet and concavo-convex or convexo-flat ultrasonic-embossed sheet.

4 Claims, 14 Drawing Sheets

ABSORBENT ARTICLE AND METHOD OF PRODUCING THE SAME

TECHNICAL FIELD

The present invention relates to an absorbent article such as a paper diaper, a sanitary napkin, a urine pad, or an incontinence pad, and a method of producing the absorbent article. More specifically, the invention relates to an absorbent article provided with a face sheet and an absorbent body in this order, and a method of producing the absorbent article.

BACKGROUND ART

The absorbent articles of this kind include (1) articles produced by covering the surface of an absorbent body with a face sheet, (2) as a modification thereof, articles that are improved in diffusion properties of body fluids and have a second sheet intervened between the face sheet and the absorbent body, (3) as a modification thereof, articles that are improved in prevention of wrinkles of the face sheet and have the face sheet and the second sheet affixed by an adhesive such as a hot melt, and the like (e.g., see Patent Documents 1 and 2).

However, in these absorbent articles of items (1) to (3), the face sheet is rubbed with the skin of users, so that skin roughs such as rashes are liable to be caused.

On the other hand, the methods of manufacturing an absorbent article of this kind include a method of, as shown in FIG. 6, applying embossing 103 to a face sheet 101 by means of an embossing roll 110 including, as illustrated in FIG. 5, a convex roll 111 having a plurality of convexes 113 formed on its roll surface 11a and a concave roll 112 having a plurality of concaves 114, in which the convexes 113 are fixed, formed on a roll surface 112a to thereby manufacture an absorbent article 100 provided with the face sheet 101 having the embossing 103 applied thereto and an absorbent article 102 in this order.

In the embossing roll 110 used in this conventional method, the pattern of the convex roll 111 is the same as that of the concave roll 112 and the embossing 103 is formed between the convexes 113 and their corresponding concaves 114. A skin-contacting portion 101a is formed in the embossing 103 by the mutually adjacent convexes 113 and the mutually adjacent concaves 114 that abut to the convexes 113.

However, according to this conventional method, in the face sheet 101, the area of a skin-contacting portion 101a, that is, the area of a part contacting with the skin of each user is large, so that the resulting absorbent article is liable to cause skin roughs such as rashes (e.g., see Patent Document 3).
Patent Document 1: Japanese Patent Application Laid-Open No. 2002-187228
Patent Document 2: Japanese Patent Application Laid-Open No. 2003-250836
Patent Document 3: Japanese Patent Application Laid-Open No, 9-234221

SUMMARY OF THE INVENTION

A primary object to be solved by the present invention is to provide an absorbent article where the area of a part contacting with the skin of each user is decreased, absorbency of soft feces is excellent and skin roughness is hardly caused, and to provide a method of producing the absorbent article.

The solutions solved by the invention are in the following.
An absorbent article comprising a face sheet and an absorbent body in this order, wherein the face sheet is at least one of concavo-convex or convexo-flat heat-embossed sheet and concavo-convex or convexo-flat ultrasonic-embossed sheet.

An absorbent article comprising a face sheet, a second sheet and an absorbent body in this order, wherein the face sheet is at least one of concavo-convex or convexo-flat heat-embossed sheet and ultrasonic-embossed sheet and the second sheet is at least one of concavo-convex or convexo-flat heat-embossed sheet and ultrasonic-embossed sheet while being laminated, and affixed.

An absorbent article comprising a face sheet, a second sheet and an absorbent body in this order, wherein the face sheet is at least one of concavo-convex or convexo-flat heat-embossed sheet and ultrasonic-embossed sheet, the second sheet is at least one of concavo-convex or convexo-flat heat-embossed sheet and ultrasonic-embossed sheet and the absorbent body is at least one of concavo-convex or convexo-flat heat-embossed sheet and ultrasonic-embossed sheet while being laminated, and affixed.

The absorbent article described in any one of the above, wherein the depth of the embossing is equal to or larger than the sum of the thicknesses of the embossed members.

The absorbent article described in any one of the above, wherein the area of the embossing is from 50 to 100% of the lamination area of the face sheet and the second sheet.

The absorbent article described in any one of the above, wherein the heat embossing is formed so that each emboss is narrower toward the second sheet side from the face sheet side and thus tapered downwardly.

The absorbent article described in any one of the above, wherein the heat embossing is applied at from 40 to 250° C.

(Primary Functions and Advantages of the Invention Described Above)

When the embossing is applied to the face sheet and also this embossing is concave-convex or convexo-flat, the area of a part contacting with the skin of each user is reduced. Hence, skin roughness is hardly caused.

A face sheet and a second sheet are embossed while being laminated, which affixes the face sheet and the second sheet. This prevents the face sheet from twisting on the second sheet, and thus hardly causes skin roughness attributable to the twisting of the face sheet.

A face sheet and a second sheet are embossed while being laminated, which affixes the face sheet and the second sheet. This eliminates a need to affix the face sheet to the second sheet by an adhesive, with the result of preventing the face sheet from stiffening caused by the adhesive, to thereby hardly cause skin roughness attributable to the stiffening of the face sheet.

A face sheet, a second sheet and an absorbent body are embossed while being laminated, which affixes the face sheet, the second sheet and the absorbent body. This eliminates a need to affix the face sheet, the second sheet and the absorbent body by an adhesive, with the result of preventing the face sheet and the second sheet from stiffening caused by the adhesive, to thereby hardly cause skin roughness attributable to the stiffening of the face sheet and the second sheet.

Since the face sheet is embossed, the flatness of the face sheet is reduced, resulting in decreasing the dispersion of urine and soft feces on the face sheet.

Because the depth of the embossing is equal to or larger than the sum of the thicknesses of the embossed members (the thickness summing thicknesses of respective members), the shape of the concave and the convex of the face sheet becomes sharp.

Because the embossing area is 5% or more of the lamination area (the area of a part where sheets are laminated)

of the face sheet and the second sheet, almost all the parts to which urine or soft feces are diffused are embossed.

Because the embossing is formed so that each emboss is narrower toward the second sheet side from the face sheet side and thus tapered downwardly, urine and soft feces remain in the embossing. Therefore, the contact of skin with urine or soft feces is reduced.

Because the embossing is formed so that each emboss is narrower toward the second sheet side from the face sheet side and thus tapered downwardly, urine and/or soft feces absorbed to the lower layer from the face sheet are hardly returned from the lower layer. As a result, going backward of urine and/or soft feces under loading is prevented.

The embossing roll is heated to 40 to 250° C. to make embossing, which enables application of good emboss pattern.

The solutions solved further by the invention are in the following.

A method of producing an absorbent article, comprising embossing a face sheet by means of an embossing roll including a convex roll having a plurality of convexes formed on its roll surface and a concave roll having a plurality of concaves, in which the convexes are put, formed in its roll surface to thereby produce an absorbent article provided with the embossed face sheet and an absorbent body in this order, wherein the pattern of the convex roll differs from that of the concave roll.

The method of producing an absorbent article described in the above, comprising applying, by means of the embossing roll including the convex roll in which each convex is a cone shape and the concave roll in which a boundary of mutually adjacent concaves is arranged in a lattice, embossing having a cup portion formed by the convexes and the concaves corresponding thereto and a skin-contacting portion formed by mutually adjacent convexes and the lattice portion put in between the convexes.

A method of producing an absorbent article, comprising embossing a face sheet and a second sheet by means of an embossing roll including a convex roll having a plurality of convexes formed on its roll surface and a concave roll having a plurality of concaves, in which the convexes are put, formed in its roll surface to thereby produce an absorbent article provided with the embossed face sheet, embossed second sheet and an absorbent body in this order, wherein the pattern of the convex roll differs from that of the concave roll.

The method of producing an absorbent article described in the above, comprising applying, by means of the embossing roll in which each convex is a cone shape and the concave roll in which a boundary of mutually adjacent concaves is arranged in a lattice, embossing having a cup portion formed by the convexes and the concaves corresponding thereto and a skin-contacting portion formed by mutually adjacent convexes and the lattice portion put in between the convexes.

The method of producing an absorbent article described in the above, wherein the face sheet and the second sheet may be affixed with an adhesive.

The method of producing an absorbent article described in any one of the above, wherein the relation of 30 mm ≦a width to be embossed ≦the width of the second sheet ≦120 mm ≦the width of the face sheet ≦250 mm is made to be satisfied.

The method of producing an absorbent article described in any one of the above, wherein the relations of 0.10 mm ≦the thickness of the face sheet ≦the thickness of the second sheet ≦2.50 mm and 15 g/m² ≦the basis weight of the face sheet ≦the basis weight of the second sheet ≦80 g/m² are made to be satisfied.

The method of producing an absorbent article described in any one of the above, wherein in the case where heat is applied to the convex roll and the concave roll, the relation of 0.01 mm ≦a clearance between the convex roll and the concave roll ≦the sum of the thicknesses of the face sheet and the second sheet ≦3.0 mm is made to be satisfied, The method of producing an absorbent article described in any one of the above, wherein in the case where the face sheet and the second sheet are conveyed between the convex roll and the concave roll at 100 to 250 m/min, the hydraulic pressure between the convex roll and the concave roll is set to 15 to 60 kgf.

The method of producing an absorbent article described in any one of the above, wherein heat is applied to the convex roll and the concave roll such that the relation of 40° C. <the roll surface temperature of the convex roll <the roll surface temperature of the concave roll <250° C. is satisfied.

The method of producing an absorbent article described in the above, wherein the constituent material of the face sheet and the constituent material of the second sheet are made to be identical.

The method of producing an absorbent article described in any one of the above, wherein the face sheet and the second sheet are conveyed on the convex roll and nipped and affixed using the concave roll.

The method of producing an absorbent article described in any one of the above, wherein the embossing roll does not nip a side portion with respect to an embossed part of the article.

An absorbent article produced by the method described in any one of the above.

According to the present invention, there is provided an absorbent article that hardly causes skin roughness and a method of manufacturing the article.

Best Mode for Carrying Out the Invention

Next, embodiments of the present invention will be set forth. Note that the present invention includes any of a configuration in which a face sheet is embossed (including a configuration in which a second sheet is not present), a configuration in which a face sheet and a second sheet are embossed, and a configuration in which a face sheet, a second sheet and an absorbent body are embossed. Hereinafter, as an embodiment, a configuration in which a face sheet and a second sheet are embossed (a configuration in which a second sheet is present) will be described. However, it is not intended that the present invention is limited thereto.

[Applications]

As the absorbent articles of the present invention, there can be illustrated, for example, paper diapers, sanitary napkins, urine pads, and incontinence pads. Hereinafter, as the embodiment of the present invention, for example, a case where the absorbent article is a disposable paper diaper will be described.

[Disposable Paper Diaper]

Figure 1:
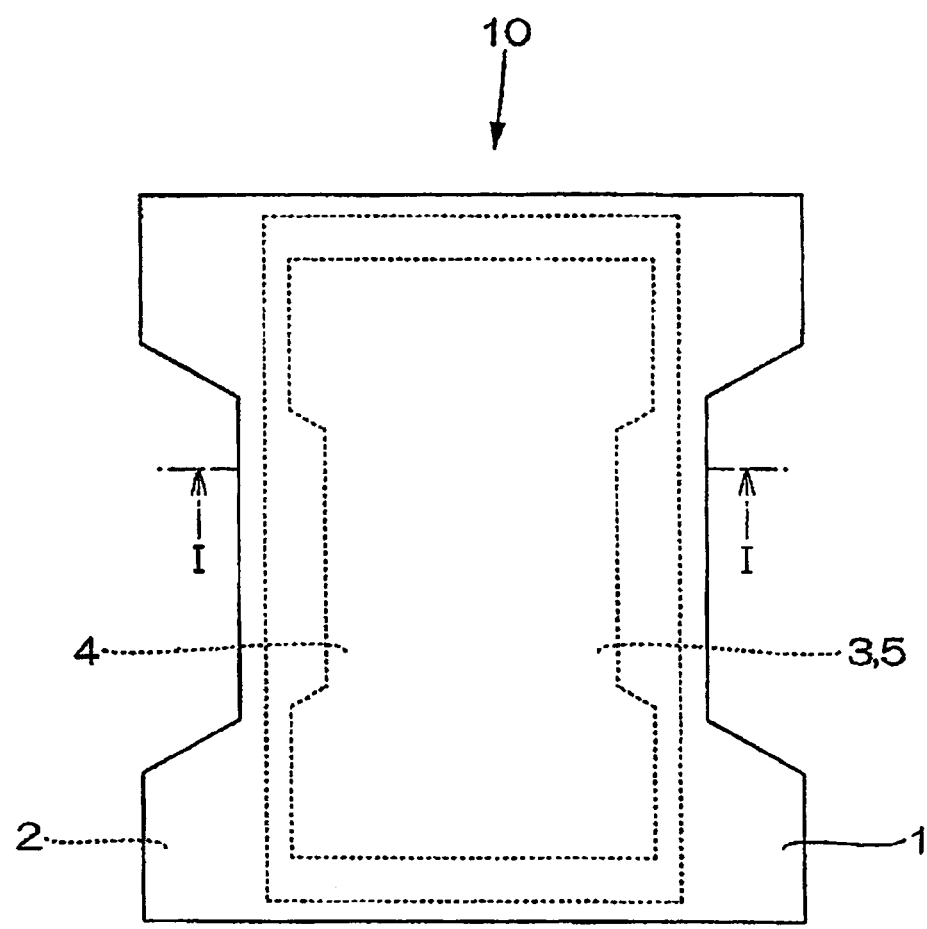
FIG. 1 is a plan view of an absorbent article.
Figure 2:
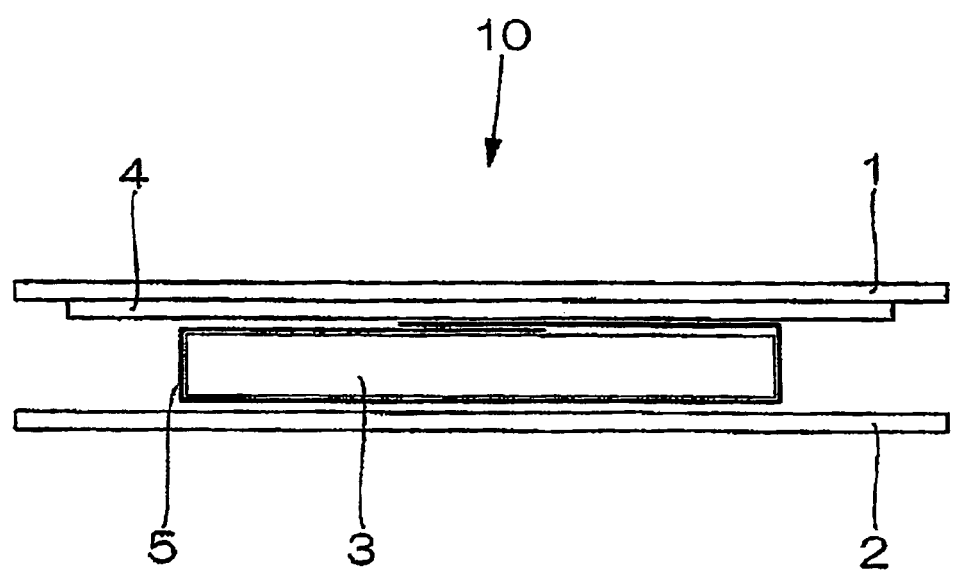
FIG. 2 is a sectional view taken along the line I-I of FIG. 1.

As shown in FIGS. 1 and 2, a disposable paper diaper 10 of the present embodiment primarily comprises a face sheet 1, a back sheet 2, an absorbent body 3 intervened between these sheets 1 and 2, and a second sheet 4 intervened between the absorbent body 3 and the face sheet 1.

The face sheet 1 and the back sheet 2 are made to form an outline of the present paper diaper 10 on its plane view, and their front and rear ends and both side ends are extended forward and rearward or laterally beyond the front and rear edges and both side edges of the absorbent body 3. The lateral extension of the face sheet 1 and the back sheet 2 is particularly long in the front and rear ends in the longitudinal direction. For example, a fastening tape (not shown) or the like is attached to this long extended part. In addition, the face sheet 1 and the back sheet 2 are affixed in such an extended part. The affixing method is not particularly limited. Available examples thereof include hot melt adhesion, ultrasonic sealing, heat sealing (heat melting), heat pressing (heat crimping) or combinations thereof. On the other hand, the absorbent body 3 as a whole is wrapped with a wrapping sheet 5 including a crepe paper, tissue paper or the like. This wrapping maintains the shape of the absorbent body 3.

Figure 3:
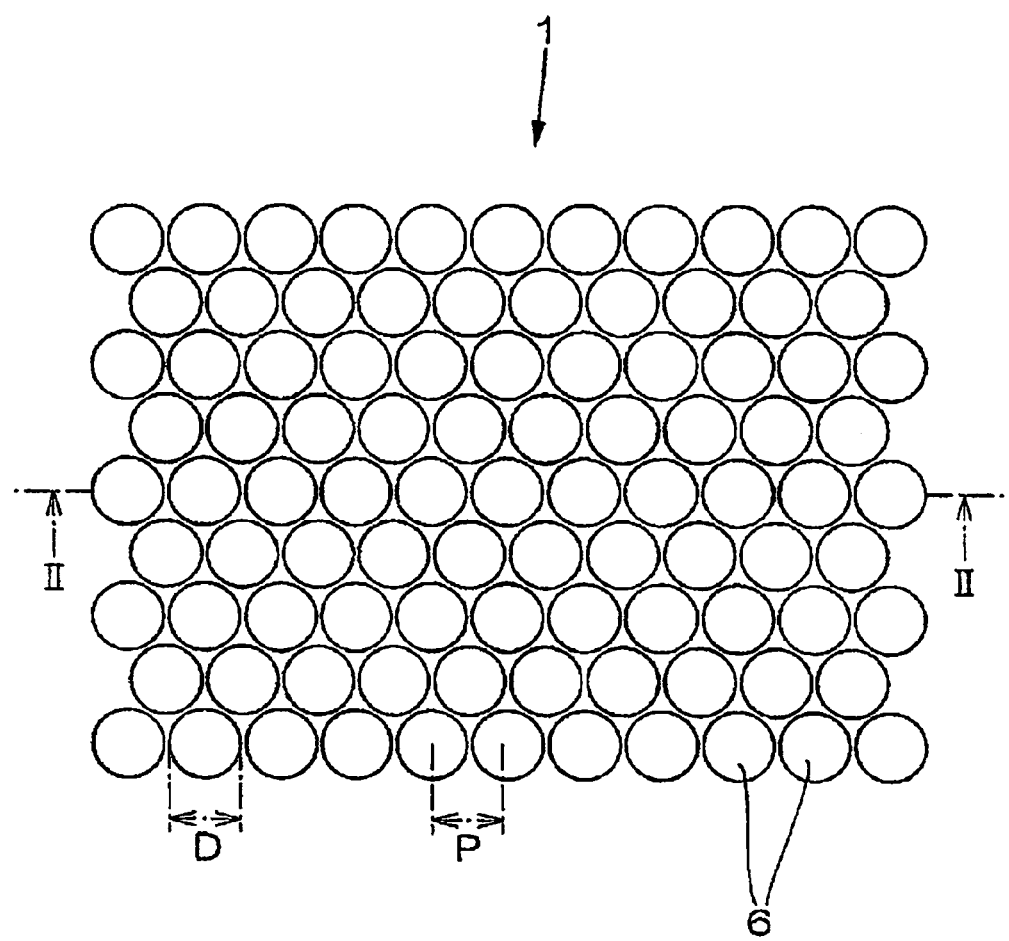
FIG. 3 is an enlarged view of a face sheet (partial).
Figure 4:
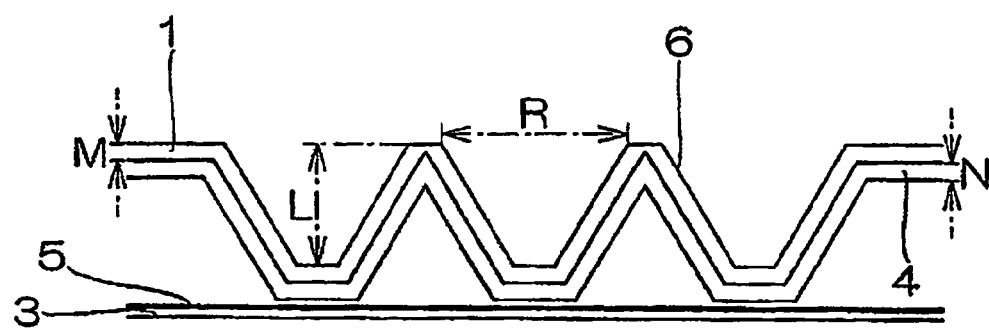
FIG. 4 is a sectional view taken along the line II-II of FIG. 3 (partial).
Figure 5:
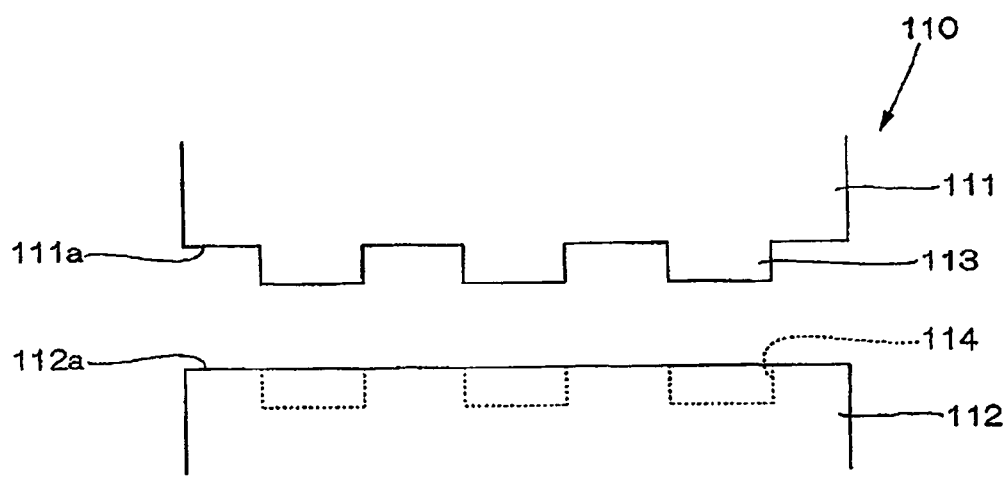
FIG. 5 is a front view of a conventional embossing roll.
Figure 6:
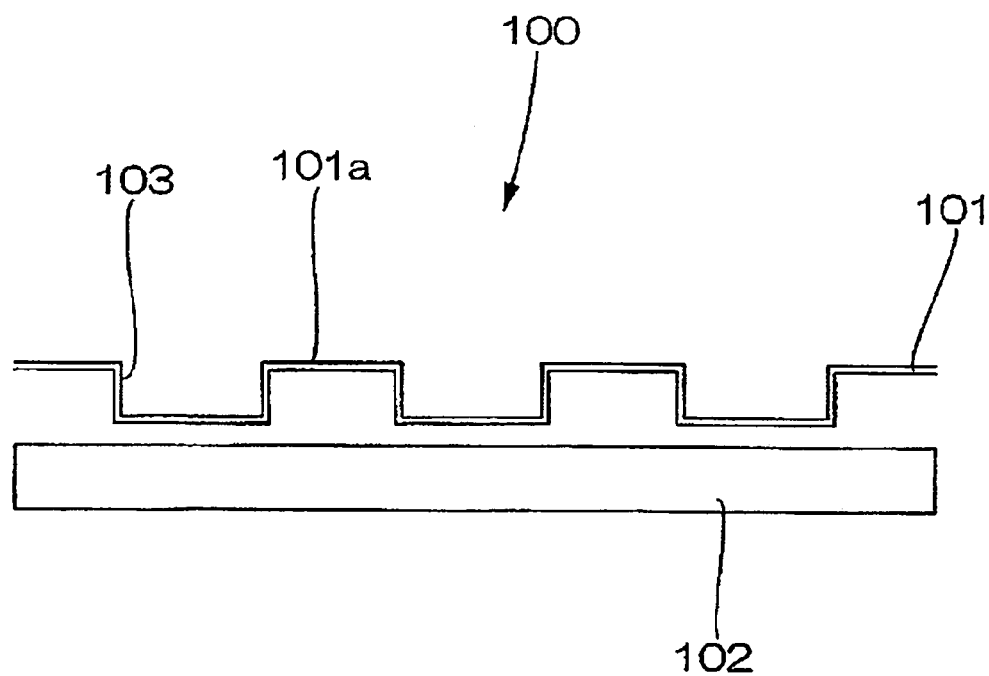
FIG. 6 is a schematic sectional view of a conventional absorbent article (a main portion).

In the paper diaper 10 of the present embodiment, for affixing the face sheet 1 and the second sheet 4, an adhesive such as a hot melt is not used. As shown in FIGS. 3 and 4, the face sheet 1 and the second sheet 4 are affixed while being laminated by applying embossing 6, which is attained by at least one of heat embossing and ultrasonic embossing. Therefore, there is no problem of stiffening of the face sheet 1 due to an adhesive which would cause skin roughness. Additionally, the application of the embossing 6 affixes the face sheet 1 to the second sheet 4, thereby not forming a space between the sheets 1, 4. Hence, body fluid is directly absorbed to the absorbent body 3, so that there is no possibility that the body fluid would remain in such a space and there is no possibility either that the remaining body fluid would go backward via the face sheet 1. Moreover, the face sheet 1 and the second sheet 4 can also be affixed with an adhesive such as a hot melt. In this case, even if they are embossed, the adhesive does not ooze out of the face sheet 1. For example, a hot melt adhesive is preferably used that has a primary component: a styrene-butadiene-styrene block copolymer and an additive: an ultraviolet absorbing agent, excluding rosin (a cause of smell) with a volatile component: 2.0% or less and exhibits an ash content: 0.5% or less, a 150° C. melt viscosity: 5000±1500 mPa·s (in accordance with JIS K-6862, 1984) and a softening degree: 84.0±7.0° C. (in accordance with JIS K-6863, 1994).

In the present embodiment, the embossing 6 is concave-convex or convexo-flat. Thus, in the face sheet 1, the area of a part contacting with skin of a user is decreased, which enables prevention of skin roughness.

The embossing 6 of the present embodiment can be changed as appropriate in designs of shape, depth, pitch, and the like so long as the above-described requirements are satisfied. However, the depth L of the embossing 6 is preferably made to be equal to or larger than the sum of the thicknesses of the face sheet 1 and the second sheet 4 (the sum of the thickness M of the face sheet 1 and the thickness N of the second sheet 4. In addition, in the case where the embossing 6 is applied to only the face sheet 1, it is the thickness of the face sheet 1, and in the case where the embossing 6 is applied to the face sheet 1, the second sheet 4 and the absorbent body 3, it is the sum of the thickness M of the face sheet 1, the thickness N of the second sheet 4 and the thickness of the absorbent body). This is for sharpening and maintaining the shape of the embossing. For example, when the thickness M of the face sheet 1 is from 0.1 to 0.7 mm, and the thickness N of the second sheet 4 is from 0.1 to 1.0 mm, the depth L of the embossing 6 can be made to be from 0.2 to 1.7 mm, preferably from 0.25 to 4.0 mm.

In addition, the area of the embossing 6 is preferably made to be from 5 to 100%, more preferably from 25 to 80%, of the lamination area (area of a part where sheets are laminated) of the face sheet 1 and the second sheet 4. When the area of the embossing 6 is made to be 5% or more of the lamination area of the face sheet 1 and the second sheet 4, the diffusion of urine or soft feces is decreased in the face sheet 1. Additionally, as illustrated in FIG. 1, in the present embodiment in which the second sheet 4 is totally covered with the face sheet 1, the lamination area in the case of a 100% embossing area is equal to the area of the second sheet 4.

Moreover, the embossing 6, as shown in FIG. 4, is preferably formed so that each emboss is narrower toward the second sheet 4 side from the face sheet 1 side and thus tapered downwardly. When the heat embossing 6 is formed so that each emboss is narrower toward the second sheet 4 side from the face sheet 1 side and thus tapered downwardly, urine and soft feces are accumulated in the heat embossing 6. Thus, the contact of skin with urine or soft feces is decreased. In addition, when the embossing 6 is formed so that each emboss is narrower toward the second sheet 4 side from the face sheet 1 side and thus tapered downwardly, urine or soft feces absorbed to the lower layer from the face sheet 1 are hardly returned from the lower layer. As a result, going backward of urine or soft feces under loading is prevented.

When the embossing 6 is tapered downwardly, a diameter D can be made to be from 1.0 to 5.0 mm, preferably from 1.8 to 3.6 mm, and a pitch P can be made to be from 1.0 to 5.0 mm, preferably from 2.5 to 3.5 mm.

Additionally, when the embossing 6, whether or not tapered downwardly, is attained by heat-embossing, it is preferably applied at 40 to 250° C., more preferably at 80 to 250° C. When the embossing temperature is lower than 40° C., a sufficient emboss pattern is not obtained, while when the temperature exceeds 250° C., the sheet is hardened. Moreover, when a sheet is heat-embossed at 80° C. or more, a low melting point fiber such as CO-PP is not completely molten, and the surface layer of the fiber is molten, whereby the surface layers of the fibers are affixed to each other. Further, when a sheet is heat-embossed at 250° C. or less, high melting point materials such as PET and acetates are also molten only in their surface layers, whereby the fibers are affixed to each other.

In order to obtain a soft sheet, a polyolefin, particularly polyethylene or polypropylene is preferably used as the raw material fiber of a sheet to be embossed. Since these resins have melting points generally ranging from 100 to 170° C., the embossing temperature is preferably from 80 to 180° C. when unwoven cloth formed by a fiber having the resin as a raw material or formed by a fiber from a composite of the fibers is embossed. In addition, for attaining both of good adhesion and softness of the face sheet and the second sheet, the sheets are particularly preferably embossed at 100 to 130° C.

[Method of Manufacturing Disposable Paper Diaper]

Figure 7:
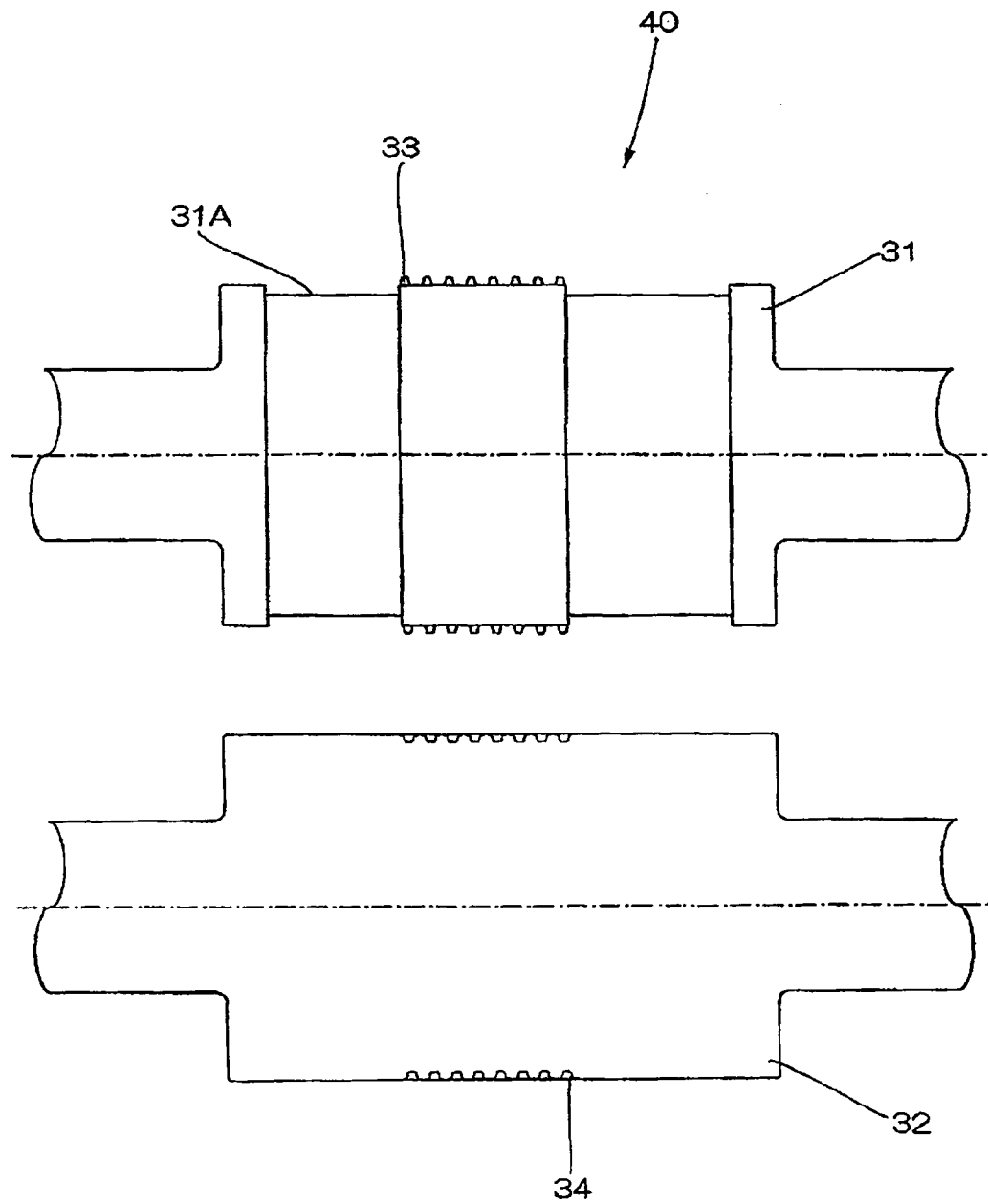
FIG. 7 is a front view of an embossing roll of the present embodiment.

In the manufacturing method of the present embodiment, the face sheet 1 and the second sheet 4 are embossed by an embossing roll 40 including a convex roll 31 having a plurality of convexes 33 formed on its roll surface and a concave roll 32 having a plurality of concaves 34, in which the convexes 33 are put, formed in its roll surface, as shown in FIG. 7. Then, the pattern of the convex roll 31 differs from that of the concave roll 32 in the embossing roll 40. This enables, in the face sheet 1 and the second sheet 4, decrease of the area of the parts contacting with the skin of each user, so that the resulting absorbent article such as the disposable paper diaper 10 hardly causes skin roughness such as a rash. Herein, the fact that the pattern of the convex roll 31 differs from that of the concave roll 32 means that the pattern shape of the convex roll 31 is different from the pattern shape of the concave roll 32 (one roll may be a plane (flat)).

Figure 8:
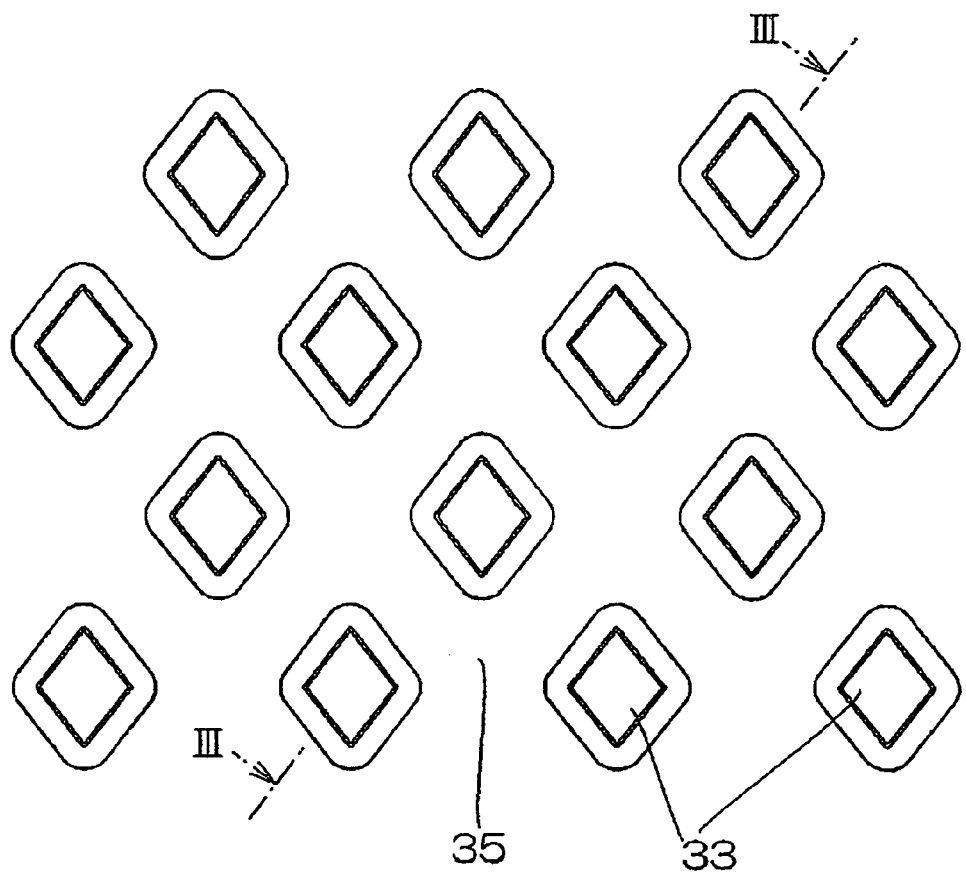
FIG. 8 is a plan view of a convex roll of the present embodiment.
Figure 9:
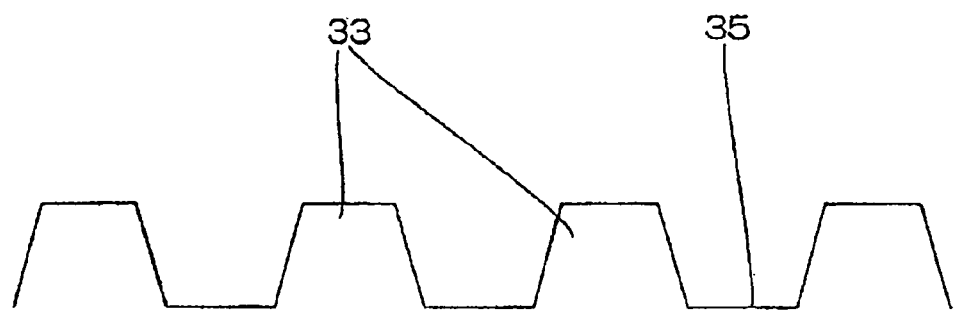
FIG. 9 is a sectional view taken along the line III-III of FIG. 8.
Figure 10:
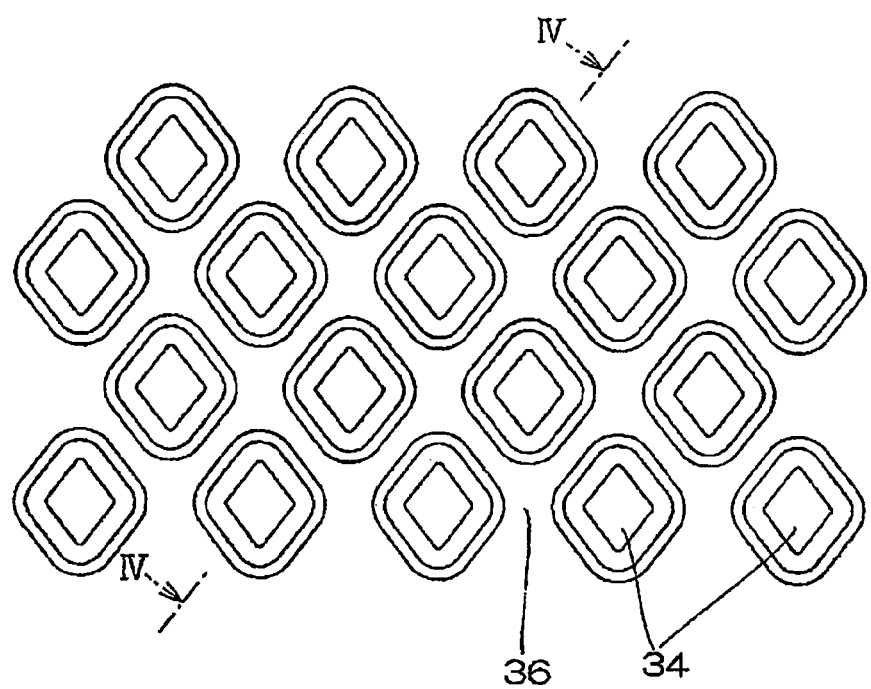
FIG. 10 is a plan view of a concave roll of the present embodiment.
Figure 11:
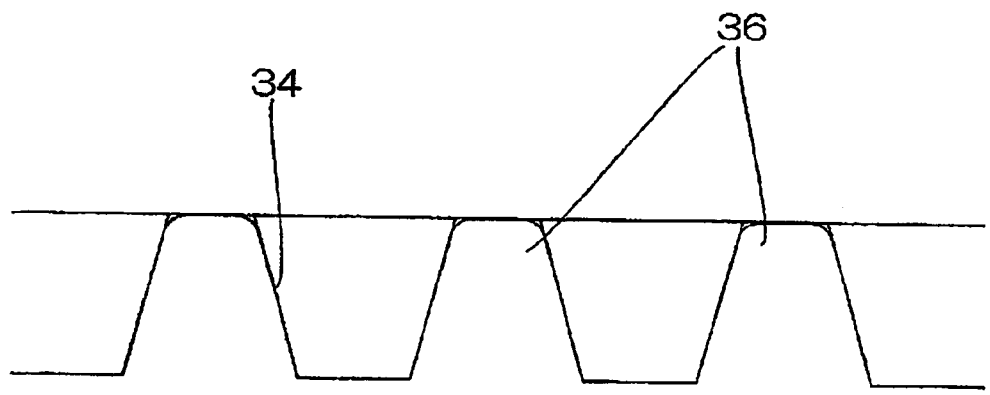
FIG. 11 is a sectional view taken along the line IV-IV of FIG. 10.
Figure 12:
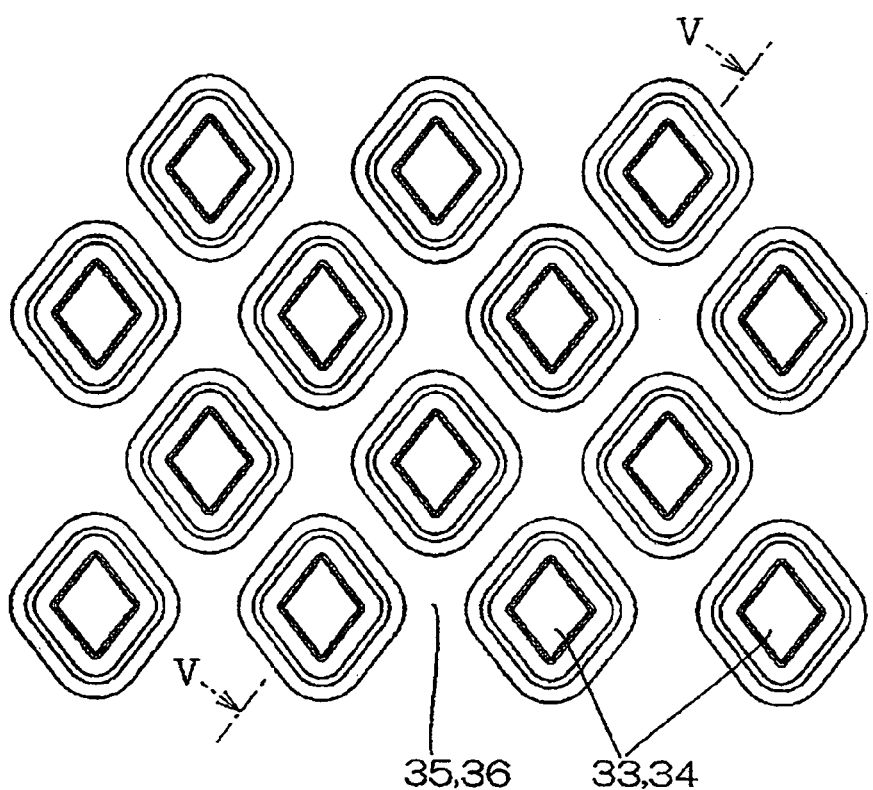
FIG. 12 is a plan view of a state in which a convex roll and a concave roll of the present embodiment are affixed together.
Figure 13:
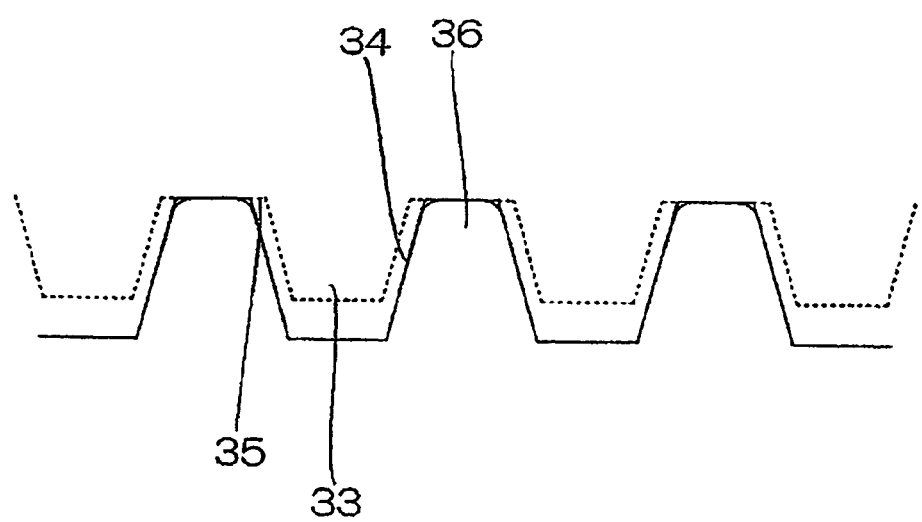
FIG. 13 is a sectional view taken along the line V-V of FIG. 12.

In the present embodiment, the pattern of the convex roll 31 differs from that of the concave roll 32 in their shapes, which are not particularly limited. However, it is preferred that, as shown in FIGS. 8 and 9, the convex 33 has a cone shape with a fore end face having the shape of a rhombus as shown in the illustrated example, or circle, elliptic, square, rectangle and so on, and the boundary of the mutually adjacent concaves 34 is arranged in a lattice (a lattice portion 36). According to this configuration, in order that the convex roll 31 and the concave roll 32 are nipped each other as illustrated in FIGS. 12 and 13 (Note that, in FIG. 13, the convex roll 31 is indicated by a dotted line, this is for showing clearly distinction between the convex roll 31 and the concave roll 32 and is not directed to a hidden line.), the face sheet 1 and the second sheet 4 are embossed so as to have a cup portion formed by the convex 33 and the concave 34 corresponding thereto and a skin-contacting portion formed by mutually adjacent convexes and a lattice portion disposed between these mutually adjacent convexes. Accordingly, the resulting absorbent article such as the disposable paper diaper 10 has the following features. Urine and soft feces are retained in the cup portion, the diffusion of urine and soft feces is inhibited due to a skin-contacting portion, and the absorbent article contacts with skin of a user only at the skin-contacting portion. Consequently, the contact area with the skin is decreased to thereby hardly cause skin roughness, and a waffle-like pattern is generated by the cup and skin-contacting portions, which brings the article soft feel.

Figure 14:
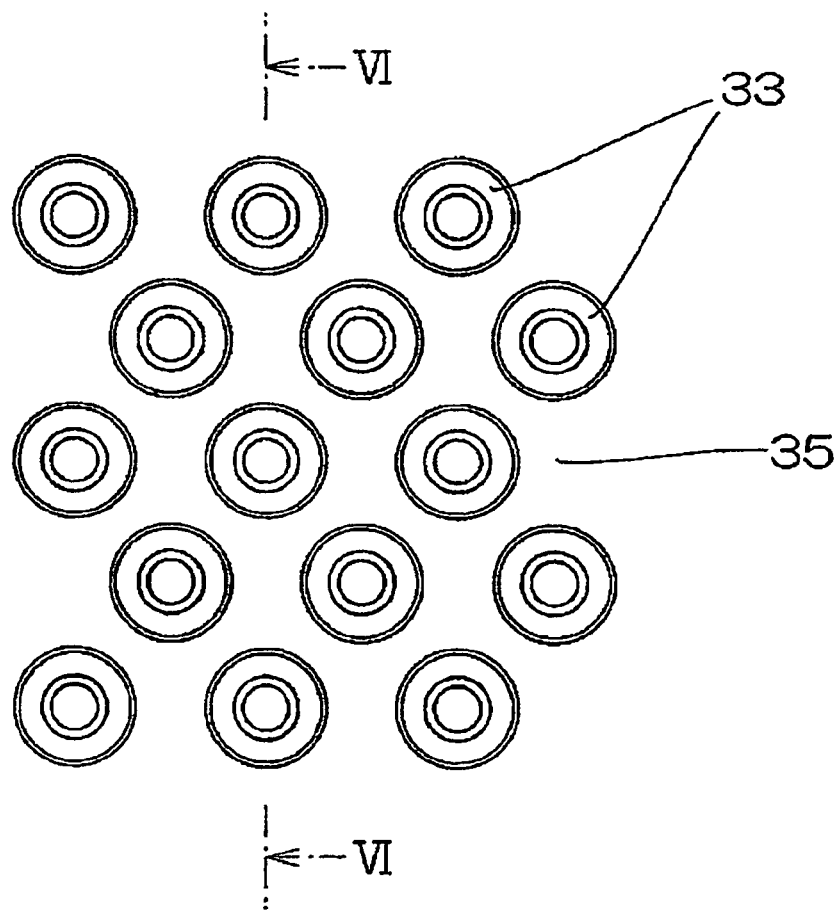
FIG. 14 is a plan view of a convex roll of the present embodiment.
Figure 15:
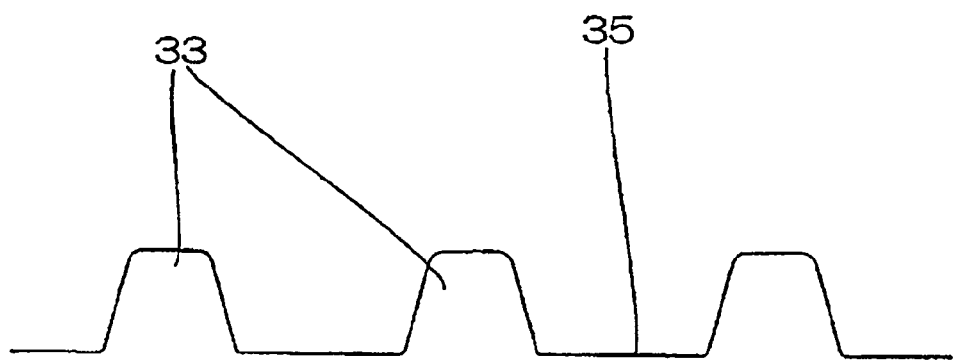
FIG. 15 is a sectional view taken along the line VI-VI of FIG. 14.
Figure 16:
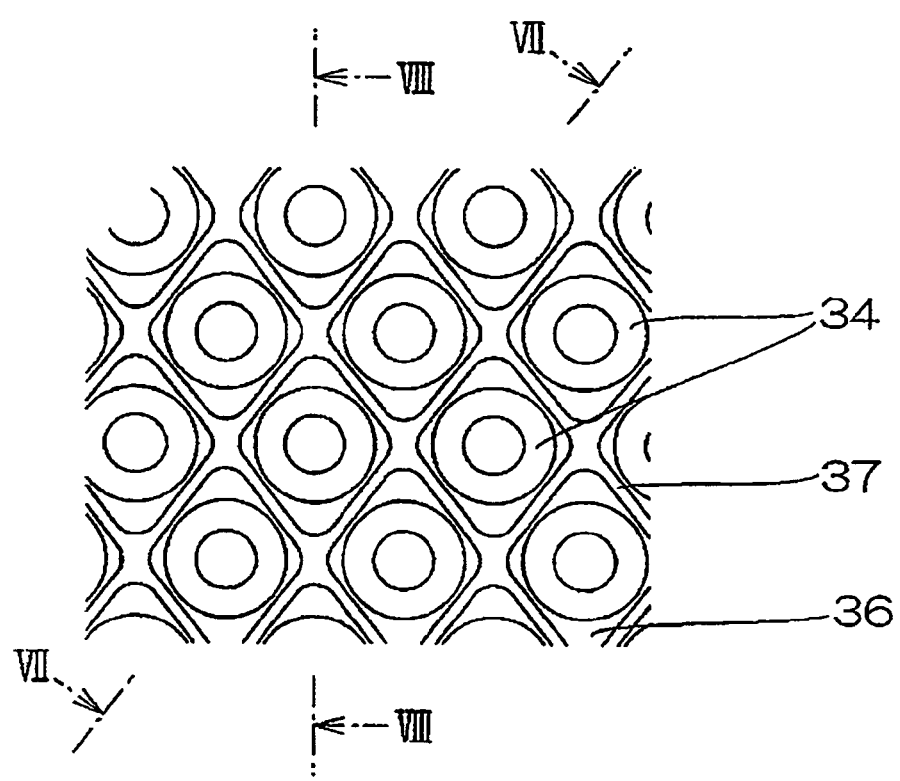
FIG. 16 is a plan view of a concave roll of the present embodiment.
Figure 17:
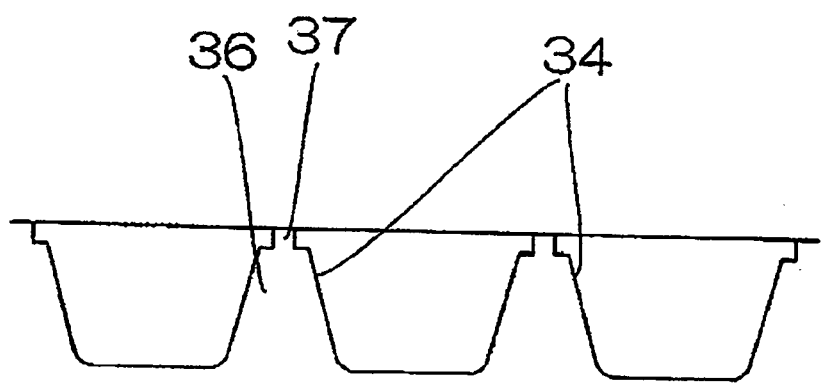
FIG. 17 is a sectional view taken along the line VII-VII of FIG. 16.
Figure 18:
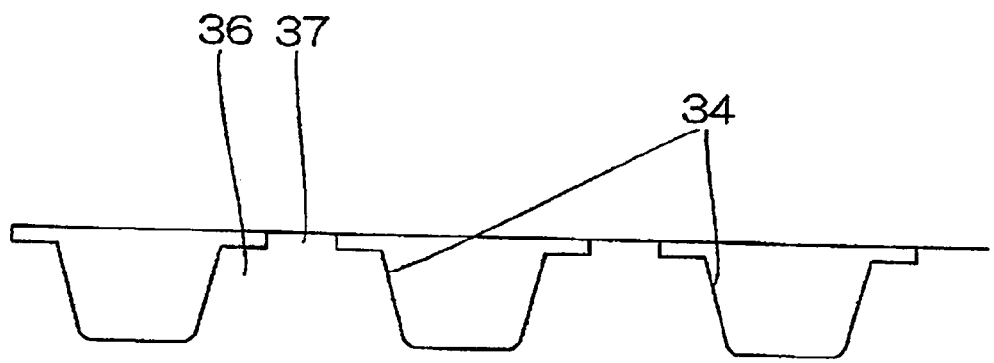
FIG. 18 is a sectional view taken along the line VIII-VIII of FIG. 16.
Figure 19:
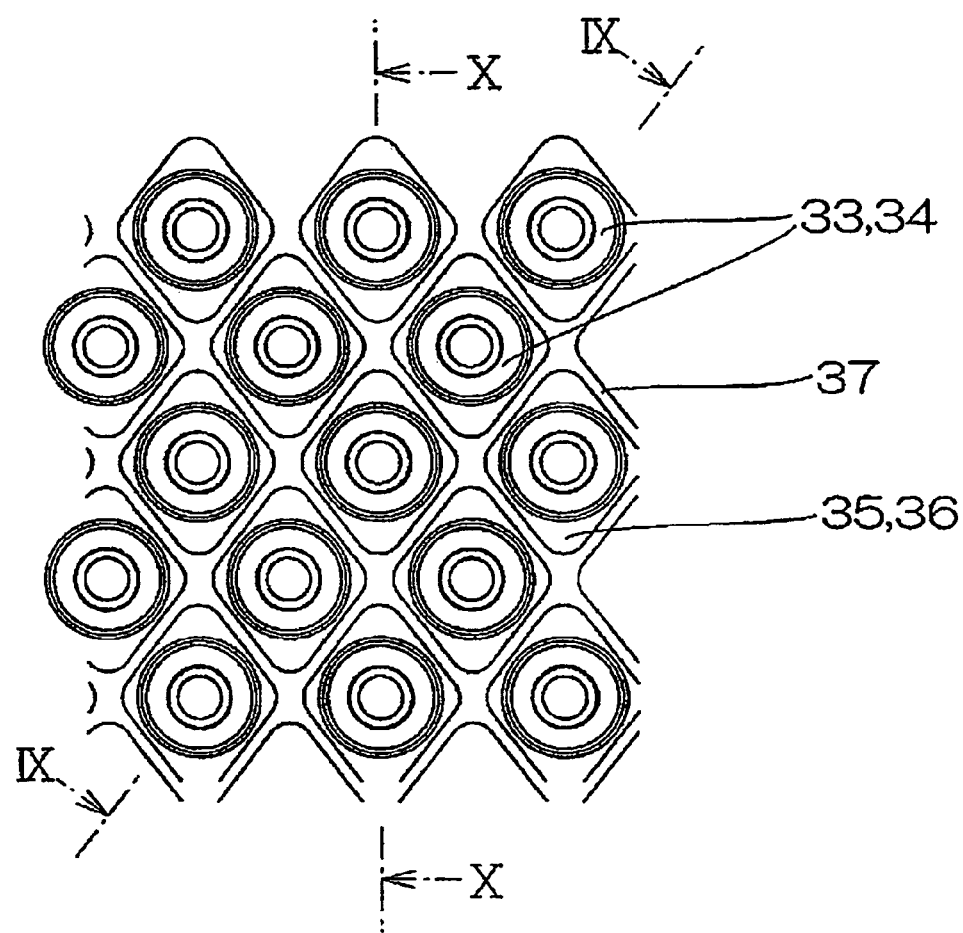
FIG. 19 is a plan view of a state in which a convex roll and a concave roll of the present embodiment are affixed together.
Figure 20:
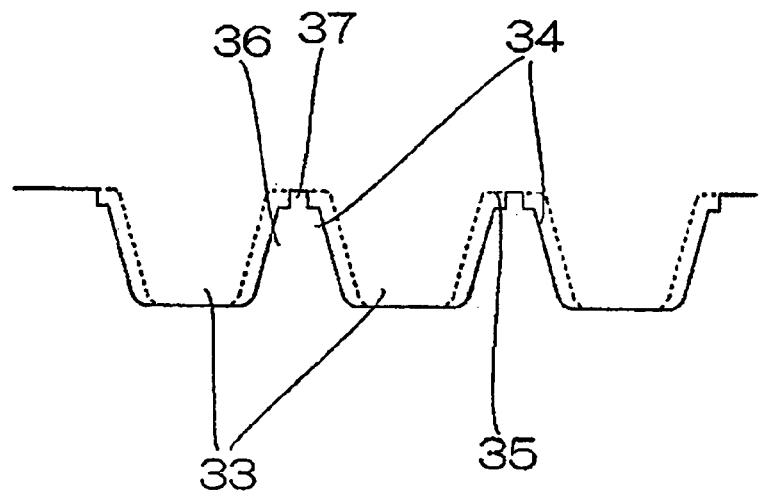
FIG. 20 is a sectional view taken along the line IX-IX of FIG. 19.
Figure 21:
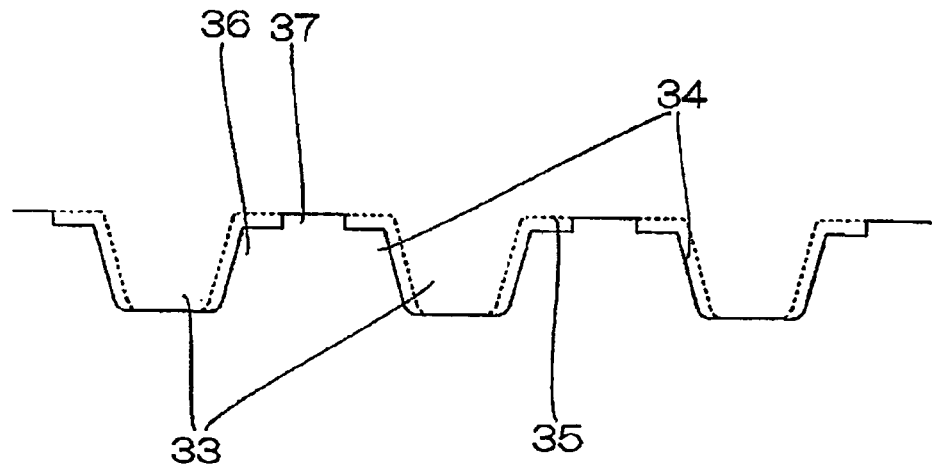
FIG. 21 is a sectional view taken along the line X-X of FIG. 19.

In addition, as a configuration in which the pattern of the convex roll 31 differs from that of the concave roll 32 as illustrated in FIGS. 14 and 15, the convex 33 preferably has a cone shape with a fore end face having the shape of circle as illustrated in these figures, or elliptic, square, rectangle rhombus and so on and as illustrated in FIGS. 16 to 18, the boundary of the mutually adjacent concaves 34 is preferably arranged in a lattice (the lattice portion 36) such as an edge line with a protrusion 37 having a narrower width disposed on the fore end face of the lattice portion 36. According to the present embodiment, the convex roll 31 and the concave roll 32 are nipped each other as shown in FIGS. 19 to 21 (Note that, although in FIGS. 20 and 21, the convex roll 31 is indicated by a dotted line, this is for showing clearly distinction between the convex roll 31 and the concave roll 32 and is not directed to a hidden line.). Hence, the embossing formed in the face sheet 1 and the second sheet 4, like the former configuration, have a cup portion formed by the convex 33 and the concave 34 corresponding thereto and a skin-contacting portion formed by mutually adjacent convexes 35 and a lattice portion 36 disposed between these mutually adjacent convexes 35, and thus have the same functions and advantages as those of the former configuration. In addition, in the present embodiment, the protrusion 37 having a narrower width is disposed on the fore end face of the lattice portion 36, whereby the area of the skin-contacting portion is more decreased, so that in the resulting absorbent article such as the disposable paper diaper 10, the area of the skin-contacting portion is more decreased, further hardly causing skin roughness. Similarly, in the present embodiment, the protrusion 37 having a narrower width is disposed on the fore end face of the lattice portion 36 to allow a skin-contacting portion to be clearly provided, which further brings the resulting absorbent article such as the disposable paper diaper 10 waffle-like soft feel. Furthermore, when the concave and the convex are made to have inverse patterns of the above case, the article contacts with the skin only at the convexes 33, whereby the area of the skin-contacting portion can be reduced to obtain a fluffy soft kilt-like pattern.

In the present embodiment, upon embossing, it is preferable to satisfy the relation of 30 mm≦the width to be embossed≦the width of the second sheet 4≦120 mm≦the width of the face sheet 1≦250 mm, and more preferable to satisfy the relation of 70 mm≦the width to be embossed≦the width of the second sheet 4≦90 mm≦the width of the face sheet 1≦180 mm. If the width to be embossed is less than 30 mm, the embossing effects (amount of absorbed feces×skin area) are hardly obtained and the strength of adhesion of the face sheet 1 and the second sheet 4 is not practically endurable (they are peeled off). The width of the second sheet 4 exceeding 120 mm is not preferable because when another sheet is adhered to the second sheet 4, strength of the adhesion part is decreased. The width of the face sheet 1 less than 120 mm is not preferable because when another sheet (a gather sheet or the like) is adhered to such face sheet 1, the adhesion is attained not easily and not surely. If the width of the face sheet 1 exceeds 250 mm, the surplus of sheet must be wrapped around the absorbent body 3 or cut off, so that the material is used wastefully.

Additionally, in the present embodiment, it is preferable to satisfy the relations of 0.10 mm≦the thickness of the face sheet 1≦the thickness of the second sheet 4≦2.50 mm and 15 g/m$^2$≦the basis weight of the face sheet 1≦the basis weight of the second sheet 4≦80 g/m$^2$, and more preferable to satisfy the relations of 0.15 mm≦the thickness of the face sheet 1≦the thickness of the second sheet 4≦2.85 mm and 20 g/m$^2$≦the basis weight of the face sheet 1≦the basis weight of the second sheet 4≦40 g/m$^2$. If the thickness of the face sheet 1 is less than 0.15 mm, it is difficult to produce unwoven cloth itself from such a thin sheet, and the roughness and fineness or light and shade unevenness inversely affects the appearance of the embossing. If the thickness of the face sheet 1 exceeds the thickness of the second sheet 4, the face sheet 1 holds urine and feces, possibly worsening absorption to the absorbent body 3. If the thickness of the second sheet 4 exceeds 2.35 mm, the basis weight is increased, thereby increasing the cost. In addition, if the basis weight of the face sheet 1 is less than 15 g/m², it is difficult to produce unwoven cloth itself from such a thin sheet, and the roughness and fineness or light and shade unevenness inversely affects the appearance of the embossing. If the basis weight of the face sheet 1 exceeds the basis weight of the second sheet 4, the face sheet 1 holds urine and feces, possibly decreasing the amount of urine and feces absorbed to the absorbent body 3. If the basis weight of the second sheet 4 exceeds 80 g/m², the cost is increased due to such high basis weight. Moreover, the thicknesses and the basis weight of the face sheet 1 and the second sheet 4 are controlled at the same time for ensuring that the appearance of the embossing is balanced with absorption.

In the present embodiment, in the case where heat is applied to the convex roll 31 and the concave roll 32 upon embossing, it is preferable to satisfy the relation of 0.01 mm≦a clearance between the convex roll 31 and the concave roll 32≦sum of the thicknesses of the face sheet 1 and the second sheet 4 (thickness of the sum of the thickness M of the face sheet 1 and the thickness N of the second sheet 4)≦3.0 mm, and more preferable to satisfy the relation of 0.05 mm≦a clearance between the convex roll 31 and the concave roll 32≦the sum of the thicknesses of the face sheet 1 and the second sheet 4≦2.5 mm. If the clearance is less than 0.01 mm, heat is applied to the whole of the face sheet 1 and the second sheet 4, so that both the sheets 1, 4 are possibly molten and hardened. Additionally, in the case of high-speed production, with such a small clearance, the convex roll 31 and the concave roll 32 are interfered with each other due to vibration, sometimes leading to the generation of unusual sounds and the breakage of facility parts. If the clearance exceeds the sum of the thicknesses of the face sheet 1 and the second sheet 4, an embossing pattern cannot be placed. If the clearance exceeds 3.0 mm, embossing may not be sharply applied and the face sheet 1 and the second sheet 4 may not be possibly heat sealed.

In addition, in the case where, upon embossing, the face sheet 1 and the second sheet 4 are conveyed through at 100 to 250 m/min between the convex roll 31 and the concave roll 32, the hydraulic pressure applied between the convex roll 31 and the concave roll 32 is preferably set to 15 to 60 kgf, more preferably 20 to 40 kgf. The hydraulic pressure is set to 15 kgf or more in order that a deflection in the embossing roll 40, which would not meet its design, is not caused by the vibration of an embossing device. On the other hand, the hydraulic pressure is 60 kgf or less for ensuring that a mechanical load for an embossing device is reduced to thereby elongate its life.

As described above, upon application of heat to the convex roll 31 and the concave roll 32, it is preferred to be 80° C.<the roll surface temperature of the convex roll 31<the roll surface temperature of the concave roll 32<250° C. If the roll surface temperature of the convex roll 31 is equal to or larger than the roll surface temperature of the concave roll 32, a shape of the convex pattern becomes too sharp and the convex pattern becomes stiff prior to putting-in of the lattice pattern.

Additionally, regardless of the roll surface temperatures of the convex roll 31 and the concave roll 32, the constituent material of the face sheet 1 is preferably made identical to that of the second sheet 4. This is because by doing so the heat seal force is increased. Herein, being identical of the constituent materials means whether or not the face sheet 1 is identical to the second sheet 4 in a broad area such as a raw material (e.g., polyester, polyethylene and the like), thickness (denier) and fiber length of each constituent fiber and a production process (e.g., span bonding or melt brown) and so on.

Embossing and lamination of the face sheet 1 and the second sheet 4 can be carried out by means of the embossing roll 40 having the convex roll 31 placed on the upper side and the concave roll 32 placed on the lower side, as illustrated in FIG. 7. Alternately, for example, a configuration is also preferred in which, by using an embossing roll including a convex roll 31 placed on the lower side and a concave roll 32 placed on the upper side, while the face sheet 1 and the second sheet 4 are conveyed on the convex roll 31, they are nipped using the concave roll 32. According to this configuration, the face sheet 1 and the second sheet 4 are lifted by the convex roll 31 and sealed by the concave roll 32, so that the face sheet 1 and the second sheet 4 become fluffy and have softness.

Moreover, upon embossing, the embossing roll does not nip a side portion with respect to an embossed part of the article. This is because it is intended that wrinkles are prevented in the side portions with respect to the embossed parts of the face sheet 1 and the second sheet 4. A manner where the side portions with respect to the embossed part are not nipped is not particularly limited. For example, the convex roll 31 and the concave roll 32 are made to have the same width as that of the embossed part, as illustrated in FIG. 7, at least either the convex roll 31 or the concave roll 32 is made to have smaller diameters at side parts 31A with respect to the embossing part of each roll, or the like.

[Material or the Like of Each Member]

(Face Sheet 1)

The face sheet 1 has properties of permeating for body fluids such as urine and blood. Thus, the material of the face sheet 1 is sufficient so long as it exhibits the body fluid permeability, and examples thereof include perforated or imperforated unwoven cloth and porous plastic sheets. Among these, as for the unwoven cloth, its raw material fiber is not particularly limited. Examples thereof include olefins such as polyethylene, polypropylene and the like, synthetic fibers such as polyesters, polyamides and the like, regenerated fibers such as rayon, cupra and the like, natural fibers such as cotton and the like, and mixed fibers using these two kinds or more. Additionally, the unwoven cloth may be produced by any processing method. Examples of the processing methods include well-known methods such as a span lace method, span bond method, thermal bond method, melt brown method, needle punch method and the like. For example, the span lace method is preferable if flexibility or drapeability is needed; and the thermal bond method is preferable if bulkiness or softness is needed.

Moreover, the face sheet 1 of the embodiment may be made up of one sheet or a laminated sheet produced by lamination of two or more sheets. Similarly, the face sheet 1 may be constituted by one sheet or by two or more sheets disposed on its plane.

(Back Sheet 2)

The back sheet 2 has properties of not permeating for body fluids. Thus, the material of the face sheet is sufficient so long as it exhibits the body fluid impermeability. Examples thereof include olefin resins such as polyethylene resin, polypropylene resin and the like, laminated unwoven cloth produced by lamination of unwoven cloth on a polyethylene sheet or the like, and unwoven cloth substantially securing impermeability by intervening a waterproof film (in this case, the back sheet 2 with the body fluid impermeability is constituted by a waterproof film and unwoven film). Of course, examples thereof include, other than these, materials recently preferably used from the viewpoint of humid prevention due to its liquid-impermeability and moisture permeability. Examples of the sheets of materials having the liquid-impermeability and moisture permeability include microporous sheets obtained by kneading an inorganic filler with an olefin resin such as polyethylene resin, polypropylene resin and the like to form a sheet and then stretching it in a uniaxial or biaxial direction.

(Absorbent Body 3)

The absorbent body 3 has properties of absorbing and retaining body fluids. Thus, the material of the absorbent body 3 is sufficient so long as it exhibits the body fluid absorption and retention. Examples thereof include well-known materials including just pulp such as cotton pulp, synthetic pulp and the like, materials obtained by mixing powdered particulates or the like of the high absorptive polymer into fluff pulp, and the like. Among these, as for the pulp, its raw material fiber is not particularly limited and examples thereof include cellulose fibers obtained from wood such as mechanical pulp, chemical pulp, dissolving pulp and the like, artistic cellulose fibers such as rayon, acetate and the like. However, for the wood as a raw material of a cellulose fiber, conifer having a longer fiber length is used rather than broadleaf tree from the viewpoints of function and price.

Furthermore, the absorbent body 3 can be formed from fiber assemblies of tow such as cellulose acetate and the like, or also from absorbent materials obtained by moving an absorbent polymer into the fiber assemblies of tow.

(Second Sheet 4)

The second sheet 4 has properties of diffusing and permeating body fluids. Thus, the material of the second sheet 4 is sufficient so long as it exhibits the body fluid diffusion and permeability, and examples thereof include materials similar to the face sheet 1. The material is preferably span lace, pulp unwoven cloth, a mixed sheet of pulp and rayon, point bond or crepe paper. In addition, the second sheet 4 is particularly preferred when its body fluid permeability is better than that of the face sheet 1 and is particularly preferred when the second sheet 4 is unwoven cloth, being smaller in fiber density than the face sheet 1, including, for example, polypropylene, polyethylene, polyethylene terephthalate, polyamide, nylon, rayon, vinylon, acryl or the like.

(Wrapping Sheet 5)

The wrapping sheet 5 has properties of permeating body fluids. Thus, like materials as illustrated as the face sheet 1 and the second sheet 4 can be exemplified.

Industrial Applicability

The present invention is applicable to an absorbent article such as a paper diaper, a sanitary napkin, a urine pad, or an incontinence pad, and to a method of manufacturing the absorbent article.

The invention claimed is:

1. An absorbent article comprising a face sheet, a back sheet and an absorbent body intervened therebetween, at least the face sheet being concavo-convex embossed, wherein the embossing is applied by means of embossing rolls including a convex roll having a plurality of convexes formed on a roll surface of said convex roll and a concave roll having a plurality of concaves, in which the convexes are put, formed in a roll surface of said concave roll and a space being formed between an internal surface of each of said plurality of concaves and an entire peripheral surface of each corresponding convex of said plurality of convexes due to difference between a pattern of the convex roll and that of the concave roll;

a boundary of mutually adjacent concaves in the concave roll is arranged in a lattice and the convexes in the convex roll have a cone shape with a circular fore end face and are formed so as to be narrower and thus tapered toward the fore end;

in the concavo-convex embossing, convex embossing is applied from a skin-contacting surface side of the face sheet and concave embossing is applied from a skin-non-contacting surface side; and a protrusion is disposed on the fore end face of the lattice portion of the concave roll, and the protrusion has a narrower width than a width of the fore end face of the lattice portion.

2. The absorbent article according to claim 1, wherein in the concavo-convex embossing, concave embossing is applied from a skin-contacting surface side of the face sheet and convex embossing is applied from a skin-non-contacting surface side.

3. The absorbent article according to claim 1, wherein a second sheet is intervened between the face sheet and the absorbent body, and the concavo-convex embossing is applied to the face sheet and the second sheet while they are laminated, and affixed.

4. The absorbent article according to claim 1, wherein the concave-convex embossing is applied to the face sheet and the absorbent body while they are laminated, and affixed.

* * * * *